(12) United States Patent
Belhe et al.

(10) Patent No.: US 7,122,034 B2
(45) Date of Patent: Oct. 17, 2006

(54) CURVED ABLATION CATHETER

(75) Inventors: Kedar Ravindra Belhe, Minnetonka, MN (US); Saurav Paul, Minneapolis, MN (US); Hong Cao, Shakopee, MN (US); John Avi Roop, Crystal, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 211 days.

(21) Appl. No.: 10/856,543

(22) Filed: May 27, 2004

(65) Prior Publication Data

US 2005/0267459 A1    Dec. 1, 2005

(51) Int. Cl.
*A61B 18/18* (2006.01)
(52) U.S. Cl. .................. 606/41; 600/585; 604/95.04
(58) Field of Classification Search .................. 606/41; 600/585; 604/95.04
See application file for complete search history.

(56) References Cited

U.S. PATENT DOCUMENTS

| | | | |
|---|---|---|---|
| 5,268,316 A | | 12/1993 | Robinson et al. |
| 5,423,772 A | | 6/1995 | Lurie et al. |
| 5,445,148 A | | 8/1995 | Jaraczewski et al. |
| 5,462,545 A | * | 10/1995 | Wang et al. ................ 606/41 |
| 5,487,757 A | | 1/1996 | Truckai et al. |
| 5,549,581 A | | 8/1996 | Lurie et al. |
| 5,582,609 A | | 12/1996 | Swanson et al. |
| 5,626,136 A | * | 5/1997 | Webster, Jr. ................ 600/373 |
| 5,722,963 A | | 3/1998 | Lurie et al. |
| 5,779,669 A | * | 7/1998 | Haissaguerre et al. ... 604/95.01 |
| 5,782,828 A | | 7/1998 | Chen et al. |
| 5,807,249 A | | 9/1998 | Qin et al. |
| 5,810,802 A | * | 9/1998 | Panescu et al. ................ 606/31 |
| 5,814,029 A | * | 9/1998 | Hassett ........................ 604/528 |
| 5,823,955 A | | 10/1998 | Kuck et al. |
| 5,843,020 A | | 12/1998 | Tu et al. |
| 5,879,296 A | * | 3/1999 | Ockuly et al. ............... 600/374 |
| 5,882,346 A | | 3/1999 | Pomeranz et al. |
| 5,897,529 A | | 4/1999 | Ponzi |
| 5,916,214 A | | 6/1999 | Cosio et al. |
| 5,931,811 A | | 8/1999 | Haissaguerre et al. |
| 5,951,471 A | * | 9/1999 | de la Rama et al. ........ 600/381 |
| 5,993,462 A | | 11/1999 | Pomeranz et al. |
| 6,001,085 A | | 12/1999 | Lurie et al. |

(Continued)

FOREIGN PATENT DOCUMENTS

WO    WO 95/10319    4/1995

OTHER PUBLICATIONS

Boston Scientific—Wiseguide Guide Catheter, http://www.bostonscientific.com, depicting the allRight™ Curve; CLS™ Curve; Q-Curve®; VODA Left® Curve; SmartShapes Guide Catheter; Zone Technology; and Wire Braid Pattern, (last visited on Jul. 13, 2004).

(Continued)

*Primary Examiner*—Michael Peffley
*Assistant Examiner*—Alex Toy
(74) *Attorney, Agent, or Firm*—Heimbecher & Assoc., LLC

(57) ABSTRACT

A curved ablation catheter imparts ablative energy to target tissue, for example, along a trabecular slope, e.g., in the right atrium along the isthmus between the ostium of the inferior vena cava and the tricuspid valve. The catheter is formed with a preset curvature that, when deployed, both translates linearly and increases in radius to aid in the formation of spot or continuous linear lesions. A method of treating atrial flutter employs the curved ablation catheter.

16 Claims, 12 Drawing Sheets

U.S. PATENT DOCUMENTS

| | | | |
|---|---|---|---|
| 6,002,955 A | | 12/1999 | Willems et al. |
| 6,010,500 A | * | 1/2000 | Sherman et al. ............... 606/41 |
| 6,030,382 A | * | 2/2000 | Fleischman et al. .......... 606/41 |
| 6,045,550 A | * | 4/2000 | Simpson et al. ............... 606/42 |
| 6,080,151 A | | 6/2000 | Swartz et al. |
| 6,096,036 A | * | 8/2000 | Bowe et al. ................... 606/41 |
| 6,120,500 A | | 9/2000 | Bednarek et al. |
| 6,156,018 A | * | 12/2000 | Hassett ....................... 604/523 |
| 6,156,031 A | * | 12/2000 | Aita et al. .................... 606/33 |
| 6,200,315 B1 | * | 3/2001 | Gaiser et al. ................. 606/41 |
| 6,235,021 B1 | * | 5/2001 | Sieben ........................ 606/41 |
| 6,241,754 B1 | | 6/2001 | Swanson et al. |
| 6,264,654 B1 | | 7/2001 | Swartz et al. |
| 6,308,091 B1 | | 10/2001 | Avitall |
| 6,312,425 B1 | * | 11/2001 | Simpson et al. ............... 606/32 |
| 6,526,302 B1 | | 2/2003 | Hassett |
| 6,605,087 B1 | | 8/2003 | Swartz et al. |
| 2001/0012934 A1 | * | 8/2001 | Chandrasekaran et al. .... 606/41 |
| 2002/0019630 A1 | * | 2/2002 | Falwell et al. ................ 606/41 |
| 2002/0165534 A1 | * | 11/2002 | Hayzelden et al. ........... 606/41 |
| 2002/0188291 A1 | * | 12/2002 | Uchida et al. ................ 606/41 |
| 2003/0125730 A1 | * | 7/2003 | Berube et al. ................ 606/45 |
| 2003/0144657 A1 | * | 7/2003 | Bowe et al. .................. 606/41 |

OTHER PUBLICATIONS

Johnson & Johnson Gateway(SM), http://www.jnjgateway.com, "Vista Brite Tip" information, (last visited on Jul. 13, 2004).

Johnson & Johnson Gateway(SM), http://www.jnjgateway.com, Cordis "Vista Brite Tip Guiding Catheter" information, (last visited on Jul. 13, 2004).

Cordis Cardiology Product Catalog 2004, Vista Brite Tip Guiding Catheter, pp. D1-D6.

* cited by examiner

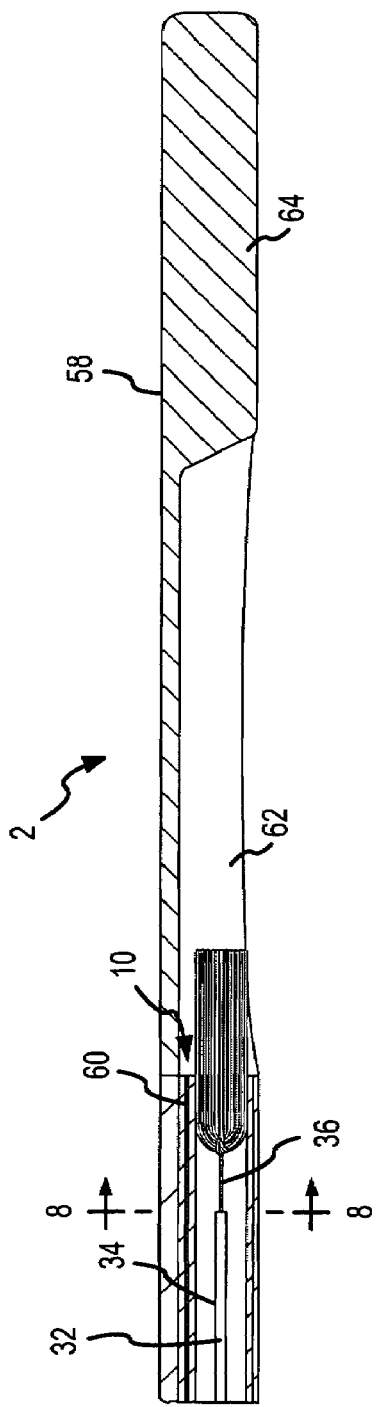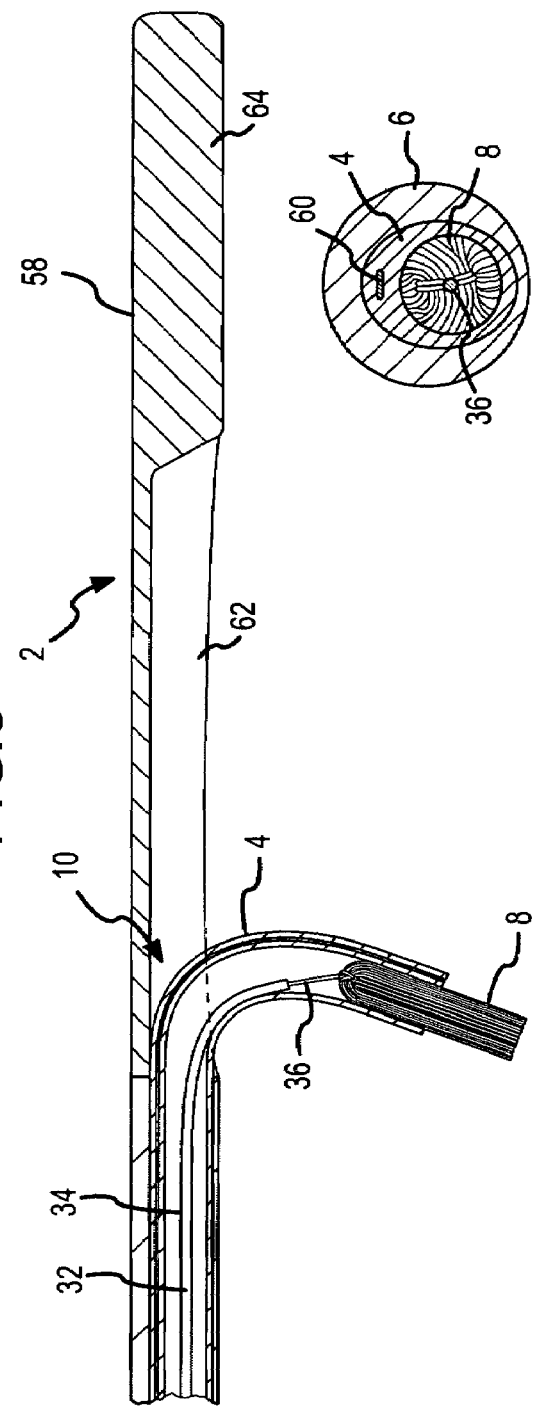
FIG.6
FIG.7
FIG.8

CURVED ABLATION CATHETER

BACKGROUND OF THE INVENTION a. Field of the Invention

The instant invention is directed toward a curved ablation catheter for imparting ablative energy (e.g., radio frequency (RF) energy) to target tissue, for example, along a trabecular slope, e.g., in the right atrium along the isthmus between the ostium of the inferior vena cava and the tricuspid valve. The catheter is formed with a preset curvature to aid in the formation of spot or continuous linear lesions.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel located near the surface of a human body and is guided to a specific location within the body for examination, diagnosis, and treatment. For example, one procedure often referred to as "catheter ablation" utilizes a catheter to convey an electrical stimulus to a selected location within the human body to create tissue necrosis. Another procedure oftentimes referred to as "mapping" utilizes a catheter with sensing electrodes to monitor various forms of electrical activity in the human body.

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well defined route which includes the His-Purkinje system into the left and right ventricles. Sometimes abnormal rhythms occur in the atrium which are referred to as atrial arrhythmia. Three of the most common arrhythmia are ectopic atrial tachycardia, atrial fibrillation, and atrial flutter. Arrhythmia can result in significant patient discomfort and even death because of a number of associated problems, including the following: (1) an irregular heart rate, which causes a patient discomfort and anxiety; (2) loss of synchronous atrioventricular contractions which compromises cardiac hemodynamics resulting in varying levels of congestive heart failure; and (3) stasis of blood flow, which increases the vulnerability to thromboembolism. It is sometimes difficult to isolate a specific pathological cause for the arrhythmia although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. Such procedures are performed many times with an ablation catheter. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the ablation procedure in the heart. The ablation catheters commonly used to perform these ablation procedures produce lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate arrhythmia.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable ventricular tachycardias and atrial flutter may be lessened or eliminated. "Sufficiently deep" lesions means transmural lesions in some cardiac applications.

One difficulty encountered with existing ablation catheters is assurance of adequate tissue contact. Current techniques for creating continuous linear lesions in endocardial applications include, for example, dragging a conventional catheter on the tissue, using an array electrode, or using pre-formed electrodes. These catheter designs either require significant technical skill on the part of the surgeon in guiding and placing the catheter by sensitive steering mechanisms. Further, all of these devices comprise rigid electrodes that do not always conform to the tissue surface, especially when sharp gradients and undulations are present, such as at the ostium of the pulmonary vein in the left atrium and the isthmus of the right atrium between the inferior vena cava and the tricuspid valve. Consequently, continuous linear lesions are difficult to achieve. With a rigid catheter, it can be quite difficult to maintain sufficient contact pressure until an adequate lesion has been formed. This problem is exacerbated on contoured or trabecular surfaces. If the contact between the electrode and the tissue cannot be properly maintained, a quality lesion is unlikely to be formed.

Thus, there remains a need for an ablation instrument that addresses these issues with the existing designs and that permits the formation of uniform spot and continuous linear lesions, including transmural lesions, on smooth or contoured surfaces, and that provides an ease of use not found in previous designs.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is an ablation catheter that is relatively simple to operate and that provides improved linear lesions. The catheter is particularly advantageous for ablating a sloped surface of endocardial tissue. The catheter has an ablation means positioned on a distal end of the catheter, a proximal section, and a resilient curved section. The curved section is proximal and adjacent to the distal end and distal and adjacent to the proximal section. The curved section is adapted to conform to a constraint, for example, an introducer sheath, that alters the curved section to assume a generally linear form, and to return to a preset curve when not otherwise constrained. When the catheter is gradually released from the constraint beginning at the distal end and progressing proximally, the curved section of the catheter progressively furls to form a hook-shape with an increasing radius of curvature to gradually assume the preset curve. Further, the distal end of the catheter translates linearly as it furls. The distal end also maintains a generally constant orientation as the catheter furls and translates and the ablation electrode thereby travels along a linear path.

In another embodiment, the invention is a device for ablating endocardial tissue. The device is composed of two main components: a sheath and a catheter. The sheath is provided for intravascular insertion into a cardiac cavity. The sheath defines a lumen, an entrance port located at a proximal end of the sheath, and an exit port located at a distal end of the sheath. The catheter is provided for insertion within the lumen of the sheath. A distal tip of the catheter has an ablation electrode and a distal portion of the catheter, proximal and adjacent to the distal tip, is adapted to resiliently retain a preset curve when not otherwise constrained. The catheter is pliant when compared to the sheath and, when residing with in the sheath, the distal portion of the catheter is constrained by the sheath. When the catheter emerges from the exit port of the sheath, the distal portion of the catheter progressively furls to form a hook-shape with an increasing radius of curvature to gradually assume the preset curve. The catheter translates linearly as it furls and the distal tip maintains an interface with and an orientation directed toward the trabecular surface as the catheter furls and translates wherein the ablation electrode is placed in contact with the endocardial tissue along a linear path.

In another aspect of the invention, a method for ablating a trabecular surface of endocardial tissue in a patient is discloses. The method is initiated by introducing a sheath defining a lumen and an exit port through a patient's vasculature into a cavity of the heart. The exit port of the sheath is then position within the heart cavity. A catheter is advanced through the lumen of the sheath to the exit port. The catheter is composed of a distal tip, an ablation electrode connected with the distal tip, a proximal section; and a resilient curved section. The curved section is proximal and adjacent to the distal tip and distal and adjacent to the proximal section. The curved section is also adapted to conform to constraint by the sheath by assuming a generally linear form and to return to a preset curve when not otherwise constrained. The catheter is gradually deployed from the sheath to allow the resilient curved section of the catheter to progressively furl into a hook-shape with an increasing radius of curvature to gradually assume the preset curve. The distal tip of the catheter is then oriented adjacent the endocardial tissue to be ablated and the ablation electrode is placed in contact with the endocardial tissue. The ablation electrode is energized. The distal tip is translated linearly as the curved section furls while contact is maintained between the ablation electrode and the endocardial tissue and a lesion is thereby created in the endocardial tissue. The sheath may further have an anchoring member, which is anchored to a wall in the heart cavity.

In another embodiment of the invention, a method is provided for treating atrial flutter in a patient. A sheath defining a lumen and an exit port is first introduced into the right atrium of the heart via the inferior vena cava. The exit port is positioned in the right atrium and a catheter is advanced through the lumen of the sheath to the exit port. The catheter is composed of an ablation electrode on a distal end, a proximal section, and a resilient curved section. The curved section is proximal and adjacent to the distal end and distal and adjacent to the proximal section. The curved section is further adapted to conform to constraint by the sheath by assuming a generally linear form, and to return to a preset curve when not otherwise constrained. The distal end of the catheter is gradually deployed from the sheath to allow the catheter to progressively furl into a hook-shape within the right atrium with an increasing radius of curvature to gradually assume the preset curve. The distal end of the catheter is oriented adjacent the isthmus between the inferior vena cava and the tricuspid valve. The ablation electrode is then placed in contact with the endocardial tissue along the isthmus and is energized. The distal end of the catheter is translated linearly as it furls while maintaining contact between the ablation electrode and the endocardial tissue along the isthmus, thereby creating a linear lesion in the endocardial tissue along the isthmus.

Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIGS. 6 and 7 are elevation views in cross-section of the embodiment of the ablation catheter and sheath of FIG. 5 in various stages of catheter deployment, wherein the catheter incorporates a wire to form a curved section.

FIG. 8 is a cross-section of the ablation catheter and sheath taken along line 8—8 of FIG. 6.

DETAILED DESCRIPTION OF THE INVENTION

Several embodiments of a curved ablation catheter 4 according to the present invention are depicted in the figures. As described further below, the curved ablation catheter 4 of the present invention provides a number of advantages, including, for example, mitigating electrode-tissue contact problems. The curved ablation catheter 4 facilitates enhanced tissue contact in difficult environments (e.g., during ablation of a contoured or trabecular surface on a beating heart), whether creating a spot lesion or a continuous linear lesion, by facilitating contact of an ablation electrode 8 with surface contours of endocardial tissue. This is particularly useful for treatment of atrial flutter where it is desirable to create a linear lesion along the trabecular slope of the isthmus between the ostium of the inferior vena cava and the tricuspid valve in the right atrium.

Figure 1:
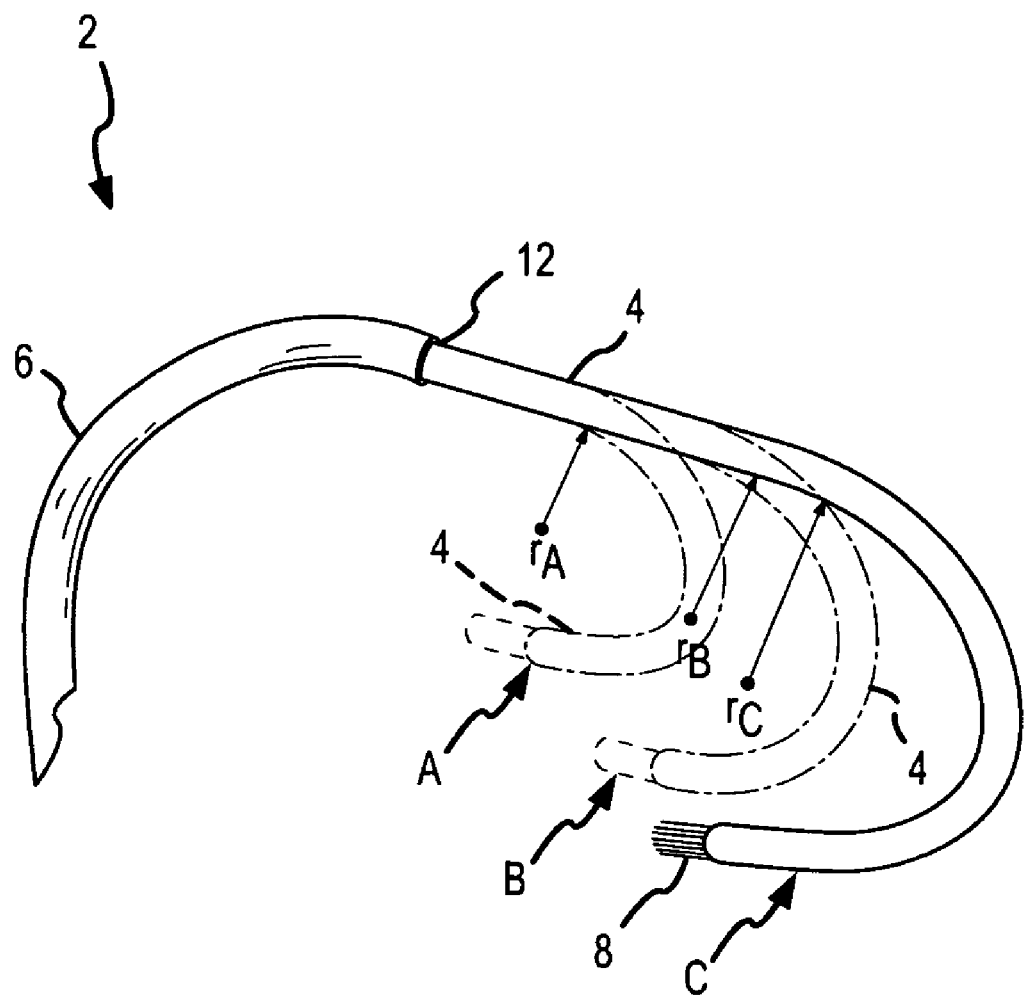
FIG. 1 is an isometric view of an ablation catheter and sheath according to one embodiment of the present invention, showing the configuration of the catheter at several stages of translation.

FIG. 1 is an isometric view of one embodiment of an endocardial ablation device 2, including a catheter 4, a sheath 6, and an ablation electrode 8. The sheath 6 defines a lumen 10 (depicted to better advantage in FIGS. 6–8), an entrance port located at a proximal end of the sheath (not shown), and an exit port 12 located at a distal end of the sheath 6. (As used herein, "proximal" refers to a direction away from the body of a patient and toward the clinician. In contrast, "distal" as used herein refers to a direction toward the body of a patient and away from the clinician.) The catheter 4 is designed for insertion within the lumen 10 of the sheath 6. Axiomatically, the diameter of the sheath lumen 10 is sized to accommodate the outer diameter of the catheter 4. The distal end of the catheter 4 is formed of a resilient material into a preset curve or hook shape. An ablation electrode 8 is joined with a distal tip 18 of the catheter 4.

Figure 2:
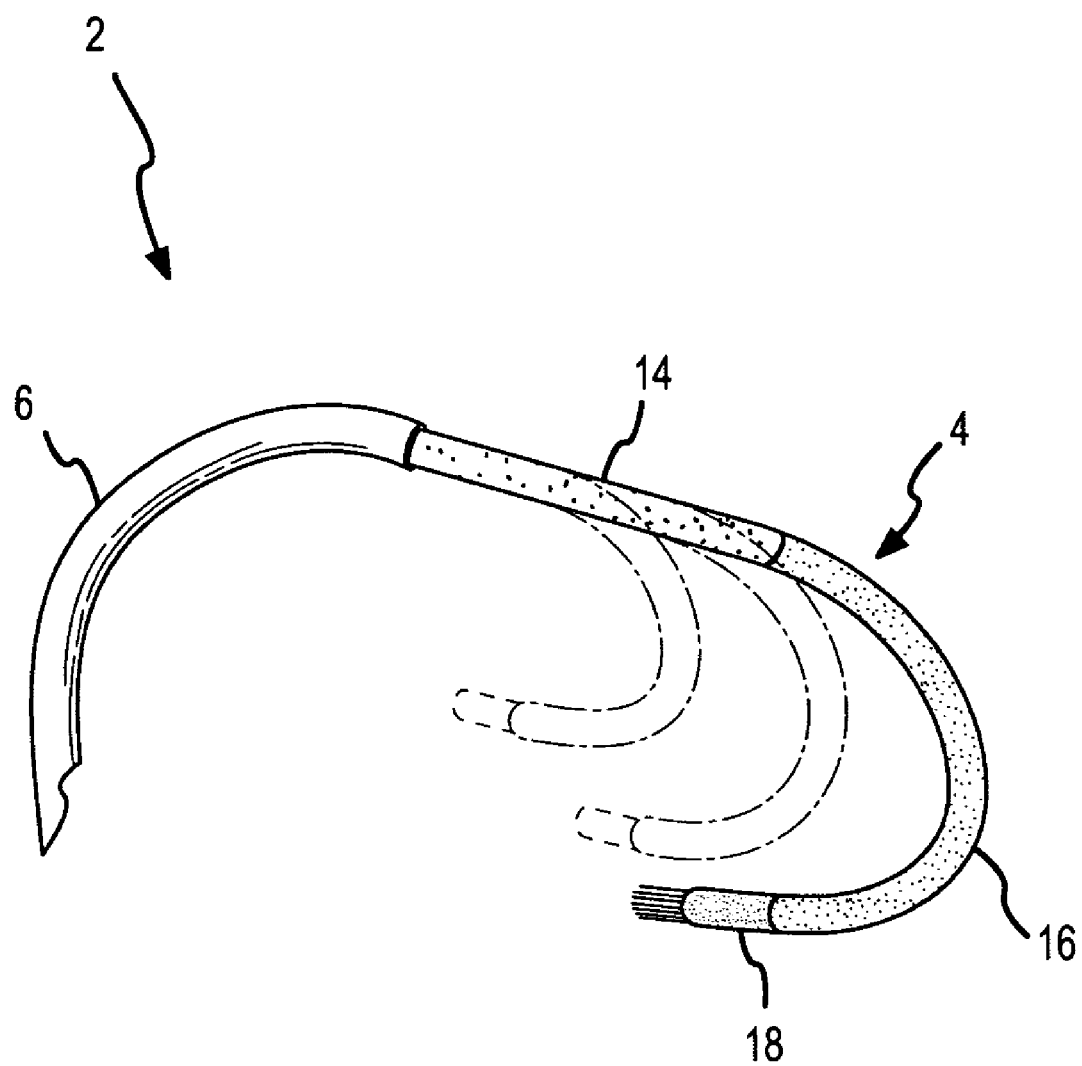
FIG. 2 is an isometric view of the ablation catheter and sheath of FIG. 1 detailing several component sections of the catheter.

As indicated, the distal end of the catheter 4, between a proximal section 14 and the distal tip 18, is formed into a curved section 16. The curved section 16 is resilient and maintains its preset hook-shape when not otherwise constrained. The curved section 16 may define an arc of between 90° and 270° or more. While the hook-shape of the curved section 16 is the normal orientation of the catheter 4, the catheter 4 is pliant compared to the sheath 6 and, when introduced into the sheath 6, the curved section 16 of the catheter 4 is constrained by the sheath 6 and may conform to a more linear orientation of the sheath 6. As depicted in FIGS. 1 and 2, when the curved section 16 of the catheter 4 is released from constraint by the sheath 4, the distal end of the catheter 4, beginning at the distal tip 18, progressively furls to form the hook-shape with an increasing radius of curvature to gradually assume the preset curve inherent in the curved section 16. This is best exemplified in FIG. 1, where as the catheter 4 progressively furls, the radius of curvature of the hook-shape at position A (shown in phantom) is $r_A$. As the catheter 4 further furls, the radius of curvature of the curved section 16 of the catheter at position B (shown in phantom) is $r_B$, which is a greater radius than $r_A$. When the curved section 16 is fully released from constraint, indicated as position C on FIG. 1, the radius of curvature is $r_C$, which is greater than $r_B$. In exemplary embodiments, the radius of curvature of the curved section 16 may be between ½ cm and 3 cm. The arc and radius of curvature of the curved section 16 may be selected to allow the catheter to appropriately "fit" in various sizes of heart cavities, to position the catheter 4 with respect to a particular tissue location for ablation application, or to orient the distal tip 18 and attached ablation electrode 8 at a particular angle or direction.

Figure 3:
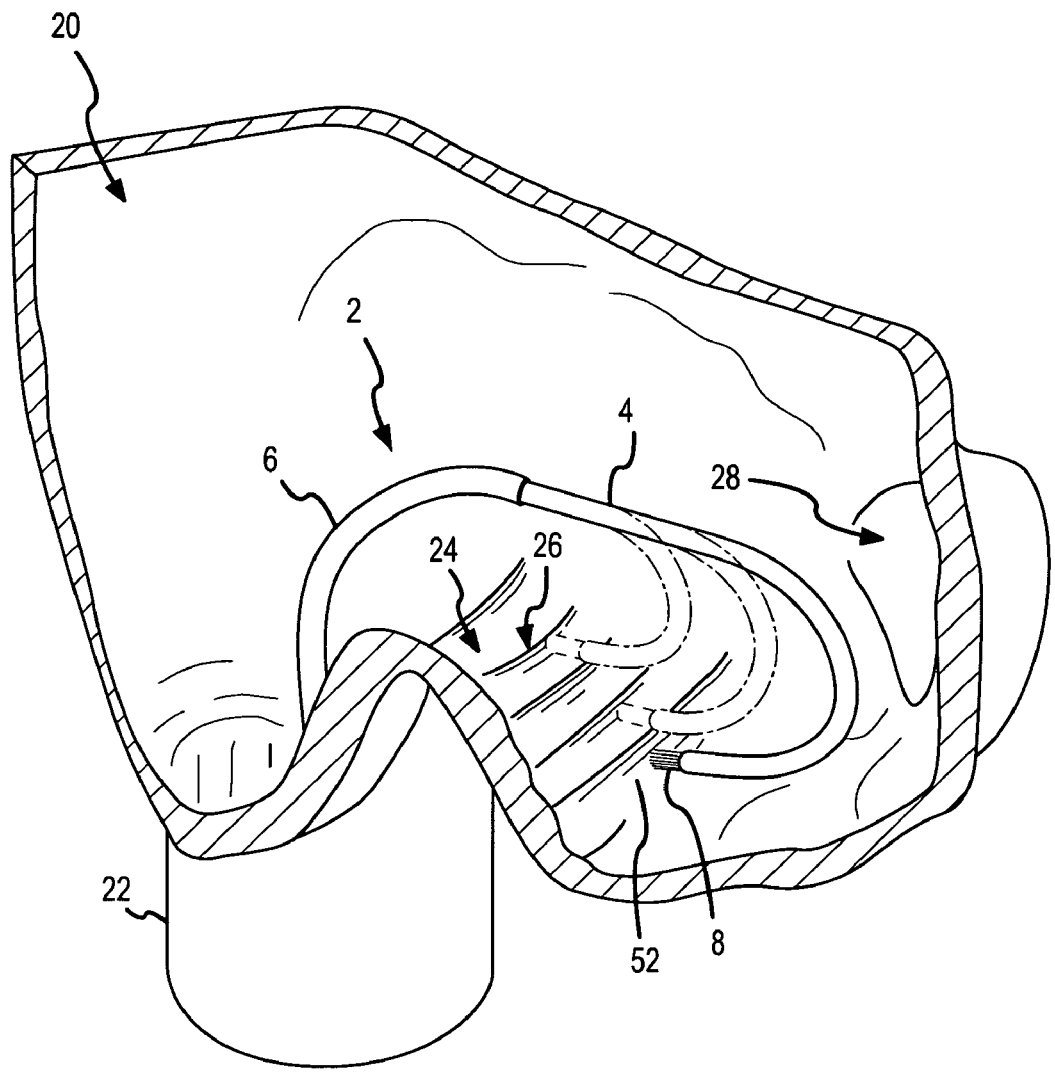
FIG. 3 is an isometric schematic of the ablation catheter and sheath of FIG. 1 depicted in situ in a right atrial cavity.

In addition, as indicated in FIGS. 1 and 2, the distal tip 18 translates linearly as the curved section 16 of the catheter 4 progressively furls. The ability of the catheter 4 to translate the distal tip 18 provides a significant advantage in the ablative treatment of certain endocardial regions. For example, as shown in FIG. 3, the endocardial ablation device 2 of the present invention provides a simple mechanism to direct an ablation electrode to treat a sloped trabecular surface 26 along the isthmus 24 between the inferior vena cava 22 and the tricuspid valve 28 in the right atrium 20. The preset curve of the curved section 16 maintains the orientation of the ablation electrode 8 toward the trabecular slope 26. Further, as the catheter 4 is deployed from the exit port 12 of the sheath 6, the radius of curvature of the hook-shape of the curved section 16 increases and the distal tip 18 translates linearly, allowing the ablation catheter 8 to contact any portion of the trabecular slope 26 desired. This is achievable by merely introducing the catheter 4 into the right atrium 20 through the sheath 6 and without extensive training by the surgeon as required in the manipulation of a steerable catheter or other similar device. Additional benefits, applications, and results are described further below.

Figure 13:
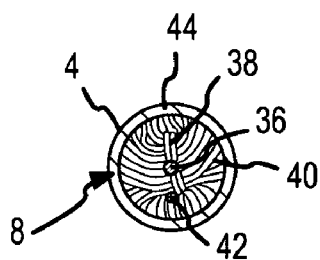
FIG. 13 is a cross-sectional view of the ablation catheter taken along line 13—13 of FIG. 12.

As depicted in FIG. 2, the catheter wall 44 may be formed from sections of different materials. For example, the catheter wall 44 may be composed of Pebax® resins (AUTOFINA Chemicals, Inc., Philadelphia, Pa.), or other polyether-block co-polyamide polymers, wherein different formulas are used to create the desired material stiffness within each section of the catheter 4. These sections of different material enable the catheter 16 to have, for example, different mechanical properties (e.g., flexibility) at different locations along the catheter shaft. For example, the proximal section 14 of the catheter wall 44 may be formed of a relatively stiffer material than the curved section 16, allowing for greater transfer of control exerted at the proximal end of the catheter 4 to the distal end. The curved section 16 may be made of a relatively more pliant material than the proximal section 14 to facilitate the formation of the hook-shape of the curved section 16, as well as provide a level of suspension to the distal tip 18 as further described below. The distal tip 18 may be of greater stiffness than the curved section 16 as well to provide appropriate support to the ablation electrode 8. The distal tip 18 may further be composed of a radiopaque marker to allow a clinician to visualize the position of the tip of the catheter 4 in the heart. In one embodiment, for example, for use in ablating within the right atrium as described in further detail herein, the length of the curved section 16 may be approximately 4 cm and the length of the distal tip 18 may be approximately 1 cm. The catheter wall 44 may or may not comprise these sections of different material depending upon the intended application for the catheter 4. Although the catheter 4 depicted in FIG. 1 (and as shown in cross-section in FIG. 13) has a circular cross section, the cross-section of the catheter wall 44 may be other than circular.

The preset curve of the curved section 16 may be formed, for example, by incorporating a wire 60 with some degree of shape-memory within the catheter 4 as shown in FIGS. 5–8. The wire 60 is oriented longitudinally along the length of the catheter 4 and may run the entire length of the catheter 60, extend only through the curved section 16 to the distal tip 18, or it may run for some intermediate length. The wire 60 may be encapsulated within the catheter wall 44 as depicted in FIG. 8, it may reside within the catheter lumen 30, or the catheter 4 may define a secondary lumen (not shown) in which the wire 60 resides. The wire 60 may be flat (as shown) to resist twisting torque that might transfer to the curved section 16 and impact the alignment.

The wire 60 may be composed of stainless steel or other material with the ability to deform and then return to a preset shape. In one embodiment, the wire 60 may be a material with a shape-memory, for example, NiTinol, a nickel-titanium (NiTi) alloy. Shape-memory metals, such as NiTinol are materials that have been plastically deformed to a desired shape before use. Then upon heat application, either from the body as the catheter is inserted into the vasculature or from external sources, the fixation element is caused to assume its original shape before being plastically deformed. NiTinol and other shape-memory alloys are able to undergo a "martensitic" phase transformation that enables them to switch from a "temporary" shape to a "parent" shape at temperatures above a transition temperature. Below that temperature, the alloy can be bent into various shapes. Holding a sample in position in a particular parent shape while heating it to a high temperature programs the alloy to remember the parent shape. Upon cooling, the alloy adopts its temporary shape, but when heated again above the transition temperature the alloy automatically reverts to its parent shape. Alternately, or in addition, shape-memory materials may also be super elastic—able to sustain a large deformation at a constant temperature—and when the deforming force is released they return to their original undeformed shape.

Common formulas of NiTinol have transformation temperatures ranging between −100 and +110° C., have great shape-memory strain, are thermally stable, and have excellent corrosion resistance, which make NiTinol exemplary for use in medical devices for insertion into a patient. For example, a catheter may be designed with a NiTinol wire with a transition temperature around or below room temperature. Before use the catheter is stored in a low-temperature state. By flushing the catheter with chilled saline solution the NiTinol wire can be kept in its deformed state while positioning the catheter for deployment at the desire site. When deployed from the sheath, the flow of chilled saline solution can be stopped and the catheter warmed by body heat, or warm saline can be substituted to allow the wire to recover its "preprogrammed" shape.

In another embodiment, the catheter itself may be composed of a shape memory material, for example, certain polymers (e.g., as available from mnemoScience GmbH, Aachen, Germany). Certain monomeric components, for example, oligo (e-caprolactone) dimethacrylate and n-butyl acrylate, when combined generate a family of polymers that display excellent shape-memory properties. Such polymers can be programmed into shape in seconds at about 70° C. and can withstand deformations of several hundred percent. In this exemplary embodiment, the oligo (e-caprolactone) dimethacrylate furnishes the crystallizable "switching" segment that determines both the temporary and permanent shape of the polymer. By varying the amount of the comonomer, n-butyl acrylate, in the polymer network, the cross-link density can be adjusted. In this way, the mechanical strength and transition temperature of the polymers can be tailored over a wide range.

Figure 9:
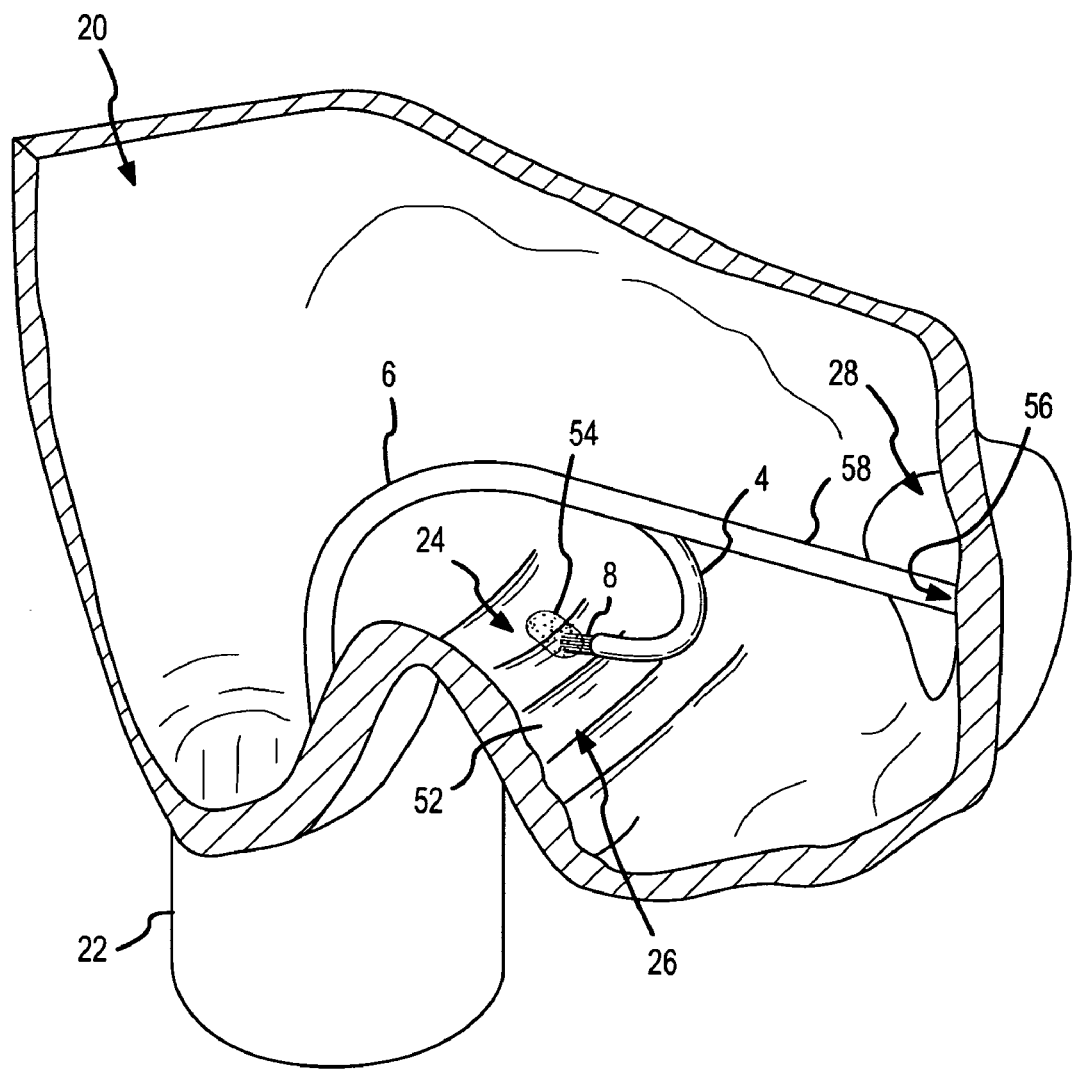
FIGS. 9–11 depict a method of using the ablation catheter and sheath of FIG. 8 to create a linear lesion in the right atrium.
Figure 10:
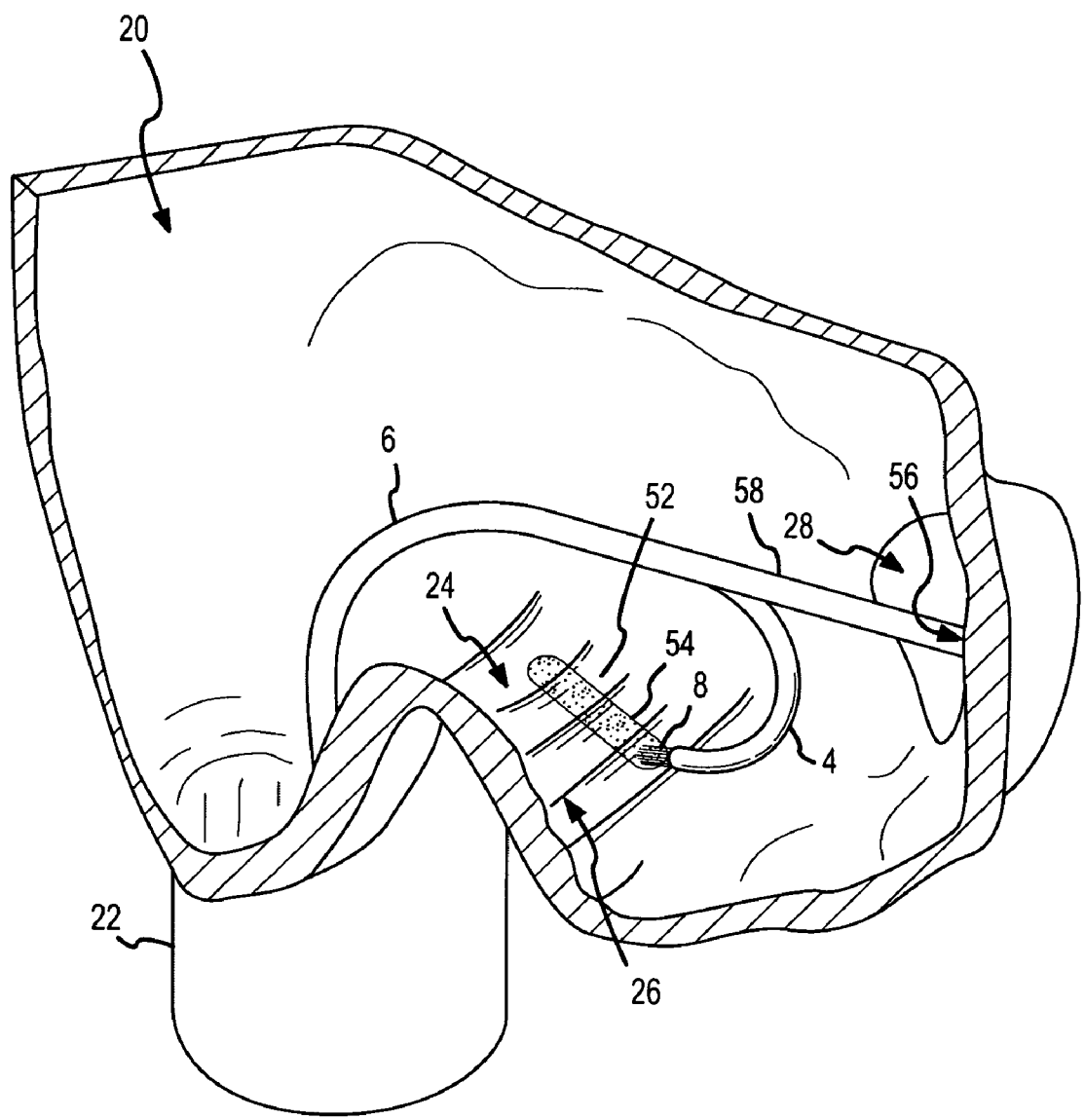
Figure 11:
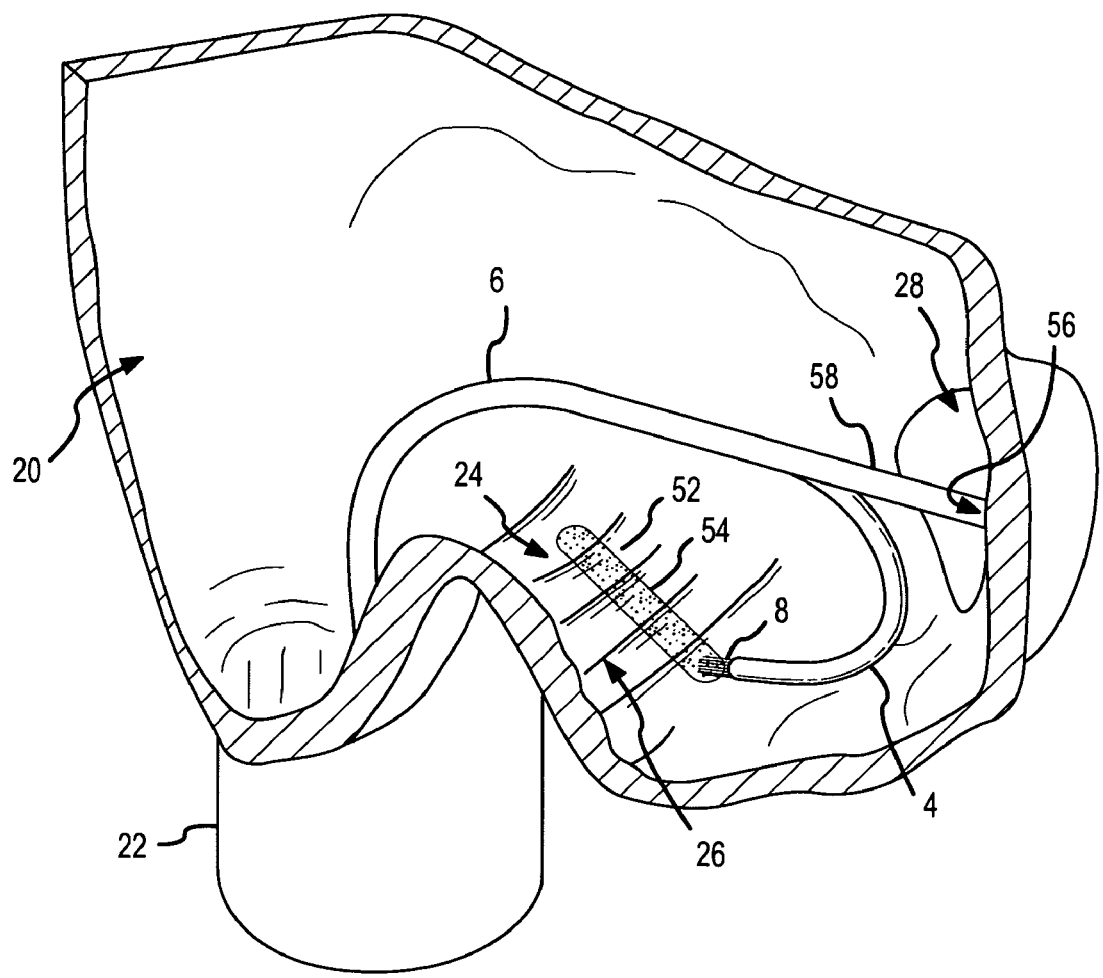

In another embodiment of the invention, the sheath 6 is formed with an anchoring member 58 at its distal end as shown in FIGS. 5–11 and 1–16. The anchoring member 58 defines a side port 62, which operates as the exit port in this embodiment. A distal finger 64 of the anchoring member 58 extends distally beyond the opening for the side port 62. The distal finger 64 may be pressed or anchored against tissue in a cavity of the heart, for example, an atrium wall 56 as shown in FIGS. 9–11, to help stabilize the endocardial ablation device 2 while the heart is beating. The anchoring member 58 may be composed of a stiffer material than portions of the sheath 6 proximal to the anchoring member 58 to facilitate stability of the anchoring member 58 to act as a platform for deployment of the catheter 4 from the side port 62. Increased stiffness of the anchoring member 58 also helps provide increased structural integrity of the sheath 6 around the side port 62 opening, as such a linear slot in the sheath 6 weakens the wall of the sheath 6. The anchoring member 58 may be composed of a polymer of greater hardness and/or stiffness than the proximal portion of the sheath 6 or it may even be composed of stainless steel or another suitable material to provide the desired rigidity and structural integrity.

Figure 5:
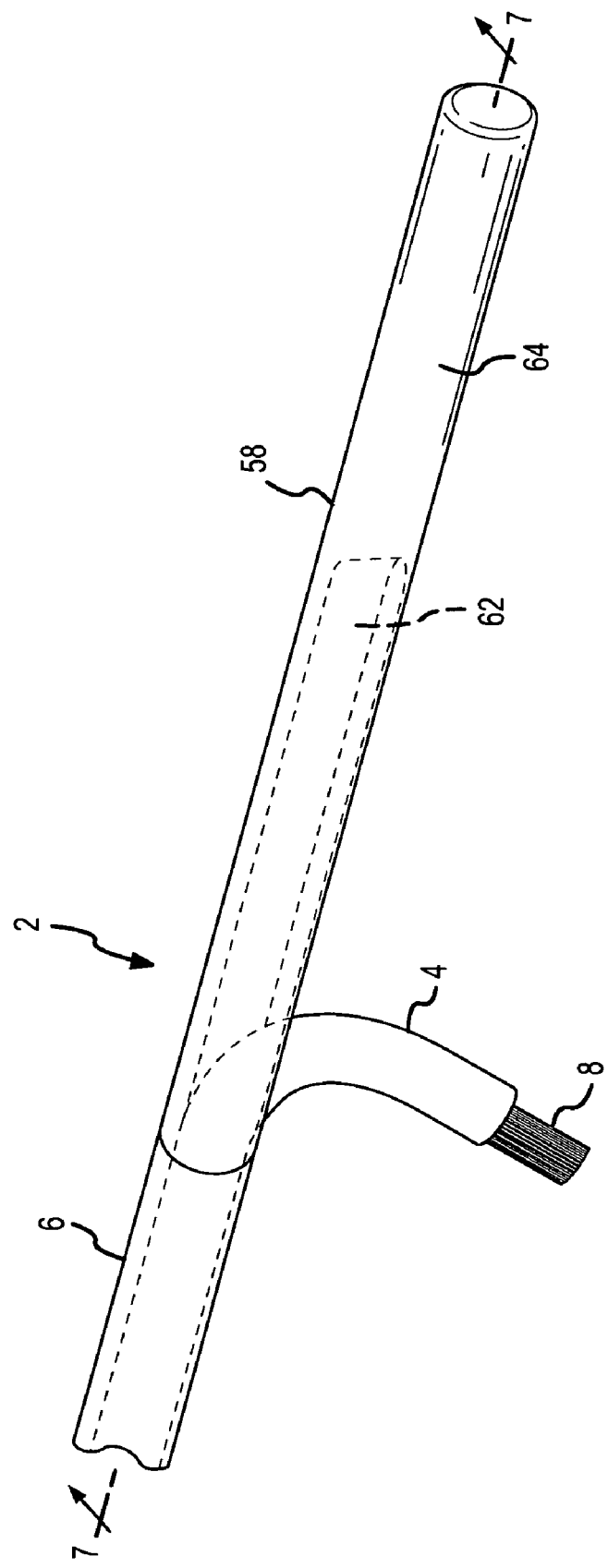
FIG. 5 is an isometric view of an alternative embodiment of the sheath wherein the ablation catheter emerges from the sheath via a side exit port.

As depicted in FIGS. 5–7, the catheter 4 begins to furl immediately upon deployment from the sheath 6 in the region of the side port 12. When the sheath 6 is positioned as desired in the heart, for example, in the right atrium as in FIG. 9 with the anchoring member set securely against the atrial wall 56, the catheter 6 is positioned on the isthmus 24 adjacent the inferior vena cava 22 with the ablation electrode 8 in contact with the tissue 52. As the catheter 4 is further deployed from the sheath 6, the curved section 16 continues to furl and also translates linearly in the direction of the anchoring member 58 as indicated by comparison of the positions of the catheter 4 in each of FIGS. 9–11. The deployment of the catheter 4 maintains the distal tip 18 and the attached ablation electrode 8 in contact with the trabecular slope 26 of the isthmus 24.

The creation of a linear lesion 54 in the tissue 52 of the isthmus 24 of the right atrium 20 is depicted schematically in FIGS. 9–11. In this procedure, a linear series of ablation lesions is created from the annulus of the tricuspid valve 28 to the inferior vena cava 22 in the isthmus 24 of right atrial tissue 52 bordering the Eustachian ridge. This isthmus 24 of tissue is critical to the large right atrial reentrant circuit responsible for atrial flutter. The ablation lesions 54 damage atrial tissue 52 preventing the conduction of electrical impulses through the critical isthmus 24. When the line of conduction block is complete, the atrial flutter circuit is shorted and the arrhythmia is cured.

As shown in FIG. 9, a linear lesion 54 is initiated by the deployment of the catheter 4 from the side port 62 of the sheath 6. The catheter 4 immediately furls as a portion of the curved section 16 emerges from the sheath 6. The furling of the curved section 16 orients the distal tip 18 toward the sloped isthmus 24 and the ablation electrode 8 is placed in contact with the tissue 52. Upon activation of a source of ablative energy connected with the ablation electrode 8, the tissue 52 is necrotized and a lesion 54 is formed. As the catheter 4 is further deployed, the distal tip 18 maintains an orientation directed toward the trabecular surface 36 of the isthmus 24 as the catheter furls and translates. The ablation electrode 8 likewise maintains an interface with the endocardial tissue 52 on the isthmus 24 along a linear path as shown in FIGS. 10–11 to create a continuous linear lesion 54.

Figure 4:
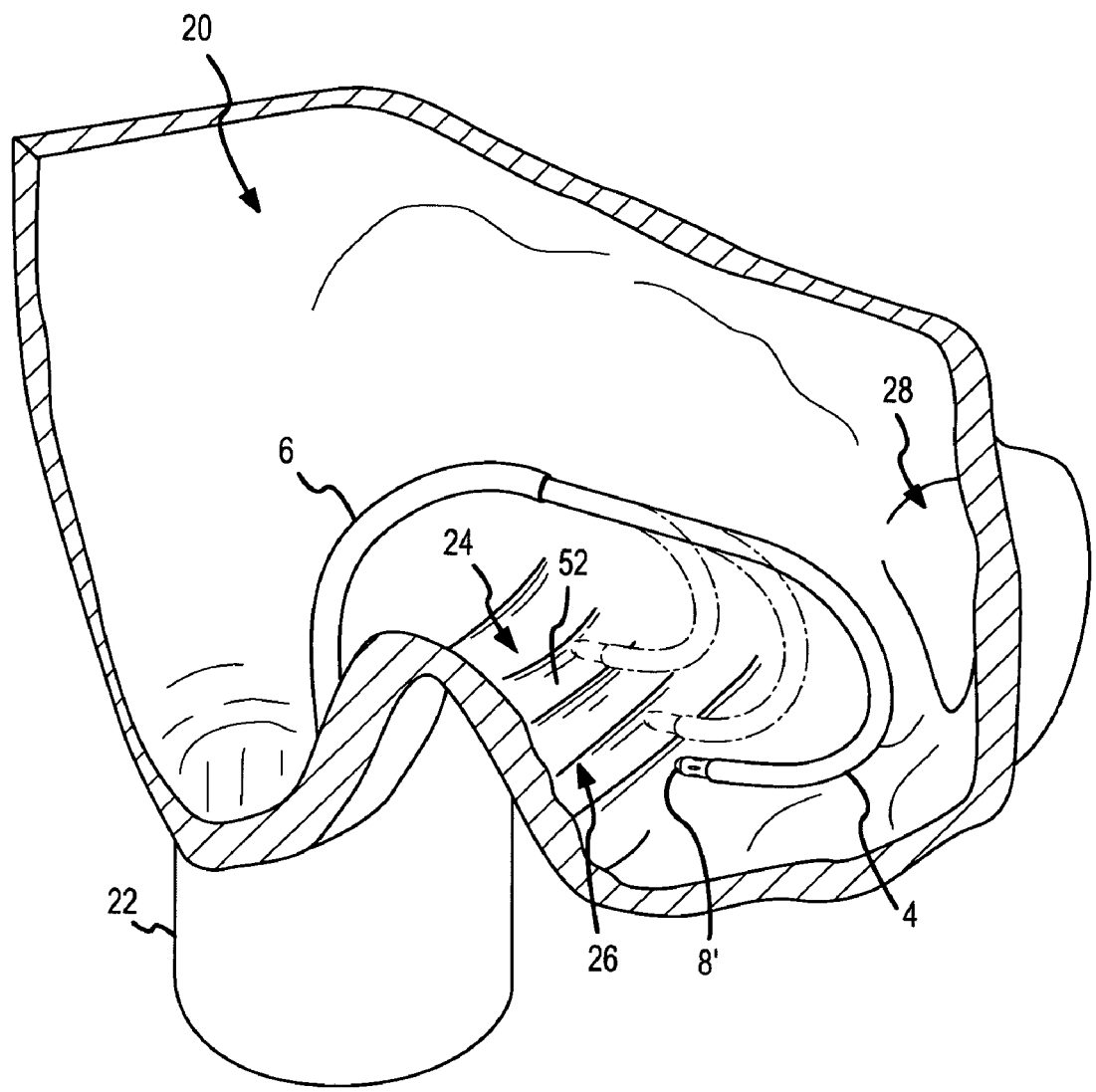
FIG. 4 is an isometric schematic of an alternate embodiment of the ablation catheter of the present invention with a ball electrode depicted in situ in the right atrium cavity.

In the particular embodiment of FIGS. 9–11, a brush electrode 8 is depicted as the ablation electrode 8. A continuous linear lesion 54 (as shown in FIG. 11) is able to be formed because of the superior ability of the filaments 40 of the brush electrode to maintain contact with the tissue 52 and to transfer ablative energy to the tissue 52. In an alternative embodiment, for example, as shown in FIG. 4, the catheter 4 may incorporate a ball electrode 8' as the ablation electrode. Although not as capable of conforming to trabecular surfaces as the brush electrode 8, the ball electrode 8' may be desired for use in certain circumstances for creating spot ablations.

The novel brush electrode 8 of the type depicted in FIGS. 1–3 and 5–14 was originally disclosed in U.S. patent application Ser. No. 10/808,919 filed 24 Mar. 2004, entitled Brush Electrode and Method for Ablation, which is hereby incorporated by reference in its entirety as though fully set forth herein. As shown in greater detail in FIGS. 12–14, the brush electrode 8 may be composed of a plurality of filaments 40, either conductive or nonconductive, arranged in a bundle and protruding from the distal tip 18 of the catheter 4. Such a flexible brush electrode 8 provides enhanced tissue contact, particularly for use on contoured or trabecular surfaces.

The filaments 40 may be constructed from a variety of different materials, including nonconductive materials, semi-conductive materials, and conductive materials. For example, the filaments 40 may be formed from metal fibers, metal plated fibers, carbon compound fibers, and other materials. Very thin, carbon fibers may be used. Relatively thicker but less conductive Thunderon® acrylic fibers (Nihon Sanmo Dyeing Company Ltd., Kyoto, Japan) may also be used for the brush electrode filaments 40. Nylon fibers coated with conductive material may also be used. Filaments 40 constructed from metal plated fibers, like coated nylon fibers, may comprise flattened areas around their outer surfaces, resulting in the filaments 40 having noncircular cross-sectional shapes. The brush filaments 40 may be insulated from each other, or they may be in electrical contact with each other. Conductive or nonconductive fluids may flow interstitially between and among the filaments 40 themselves or along the outer surface of the filaments 40.

An embedded portion 48 of the filaments 40 forming the brush electrode 8 may be contained within the catheter lumen 30 at the distal tip 18 of the catheter 4 while an exposed portion 46 may extend distally from the distal tip 18. The exposed portion 46 of the brush electrode 8 may project a few millimeters from the distal tip 18 of the catheter 4. The distance that the exposed portion 46 of the brush electrode 8 extends from the distal tip 18 of the catheter 18 varies depending upon a number of factors including the composition of the filaments 40 comprising the brush electrode 8 and the particular area to be treated with the brush electrode 8. The distal tip 18 of the catheter 4 may itself be conductive or nonconductive.

Figure 12:
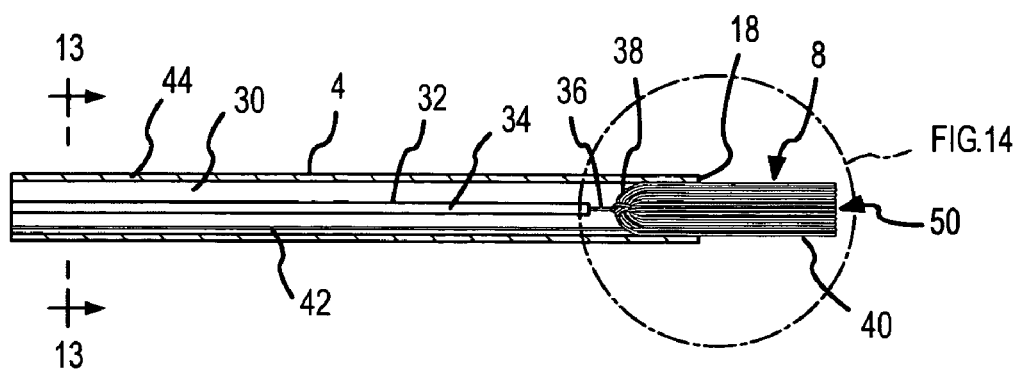
FIG. 12 is an elevation view in cross-section of the ablation catheter of FIGS. 1 and 3 embodying a brush electrode and revealing a primary conductor making electrical contact with the filaments comprising the brush electrode, and depicting a secondary lead (e.g., for a thermocouple) extending adjacent to the primary conductor and becoming embedded within the brush filaments.

FIG. 12 is a cross-sectional view of the catheter 4 of FIG. 1, for example, in a linear orientation. A primary conductor 32 having an insulated portion 34 and an uninsulated portion 36 carries ablative energy (e.g., radio frequency current) from an energy source in a controller to the brush electrode 8. The primary conductor 32 extends within the catheter lumen 30 along a longitudinal axis of the catheter 4. The primary conductor 32 may comprise, for example, insulated copper wire with an uninsulated portion 36 in electrical contact with the brush electrode 8. In this embodiment, the uninsulated portion 36 of the primary conductor 32 is formed or tied in a loop or noose 38 around the embedded portion 48 of the filaments 40 of the brush electrode 8, as shown to better advantage in FIGS. 13–14. At the loop or noose 38, ablative energy is transferred from the primary conductor 32 to the conductive filaments 40 of the brush electrode 8. In this embodiment, the uninsulated portion 36 of the primary conductor 32 is connected to the embedded portion 48 of the brush electrode 8 so that the connection between the primary conductor 32 and the brush electrode 8 is protected within the catheter wall 44. A secondary lead 42, also shown in FIGS. 12–14, may extend substantially parallel to the primary conductor 32. A distal end of the secondary lead 42 is embedded with the filaments 40 comprising the brush electrode 8. The secondary lead 60, when present, may be operatively connected to a sensor embedded in the brush electrode 8 (e.g., a thermal sensor, an ultrasound sensor, or a pressure sensor).

Figure 14:
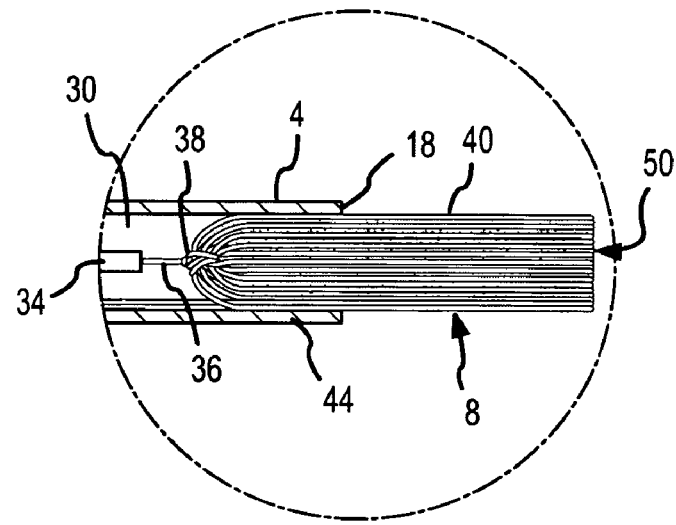
FIG. 14 is an enlarged view of the circled region of FIG. 12.

FIG. 14 is an enlarged view of the circled region of FIG. 12. As shown in FIG. 14, the brush electrode 8 may have a relatively flat working surface 50 at the distal end 32 of the brush electrode 8. In other words, in this depicted embodiment, all of the filaments 40 comprising the brush electrode 8 extend approximately the same distance from the distal tip 18 of the catheter 4. Thus, the brush tip provides a relatively flat working surface 50 comprising the longitudinal ends of the filaments 40. The catheter wall 44 at the distal tip 18 of the catheter 4 provides mechanical support for the filaments 40 and may also provide electrical shielding.

The filaments 40 may alternatively be trimmed to provide a variety of configurations and shapes for the working surface 50 of the brush electrode 8, which may provide advantages for special applications of the brush electrode 8. For example, a blade-shape may be formed by creating an edge of longer filaments of the brush electrode resulting in a line of contact with the tissue. Alternatively, the brush electrode 8 may have a wedge-shaped working surface 50 to facilitate angular placement and increase the area of the working surface 50. This configuration may be advantageous for point applications of ablative energy. As another example, the working surface 50 of the brush electrode 8 may have a concave portion or channel, which may be beneficial for wrap-around applications and provide advantages when ablating curved surfaces like the outer surface of a blood vessel. Alternatively, the working surface 50 of the brush electrode 8 may have a convex, trough-shaped tip, which may be beneficial, for example, when reaching into troughs or depressions on a contoured surface. The working surface 50 of the brush electrode 8 could also be domed, hemispherical, a frustum, or conical, coming nearly to a point at the most distal end of the brush electrode 8, with its longest filaments 40 proximal to the longitudinal axis of the catheter 4. The brush electrode 8 is depicted in many of the drawings with a circular cross section, but it may have different cross-sectional configurations.

In one embodiment, conductive or nonconductive fluid may flow through the catheter lumen 30 from a fluid source (e.g., a pump and reservoir in a controller) to the brush electrode 8. When the fluid flows through the brush electrode 8, it creates a wet-brush electrode in which impinging jets of fluid traveling interstitially impact the tissue 52 at an interface between the tissue 52 and the brush electrode 8 to help control temperature changes at the interface. When using conductive fluid and either conductive or nonconductive filaments 40, the brush electrode 8 may act as a virtual electrode. If there is no direct contact between conductive filaments and the tissue 52, or the filaments 40 are entirely nonconductive, the conductive fluid flowing through the catheter lumen 30 makes the electrical contact at the interface between the brush electrode 8 and the tissue 52.

The brush electrode 8 according to the present invention delivers ablative energy to the tissue via the conductive filaments 40 alone, via the conductive fluid alone, or via both the conductive filaments 40 and the conductive fluid. In the latter two configurations, the brush electrode 8 is referred to as a wet-brush electrode. Since it is possible for the conductive fluid to escape from the exposed portion of the wet-brush electrode prior to reaching the working surface 50 at the distal tip of the wet-brush electrode, there is some ablative energy leakage to the surrounding blood. The leakage of ablative energy to the surrounding blood is in part due to direct contact between the blood and the conductive filaments and in part due to the conductive fluid escaping between the filaments 40 to the surrounding blood, particularly when substantial splaying of the filaments 40 occurs.

Figure 15:
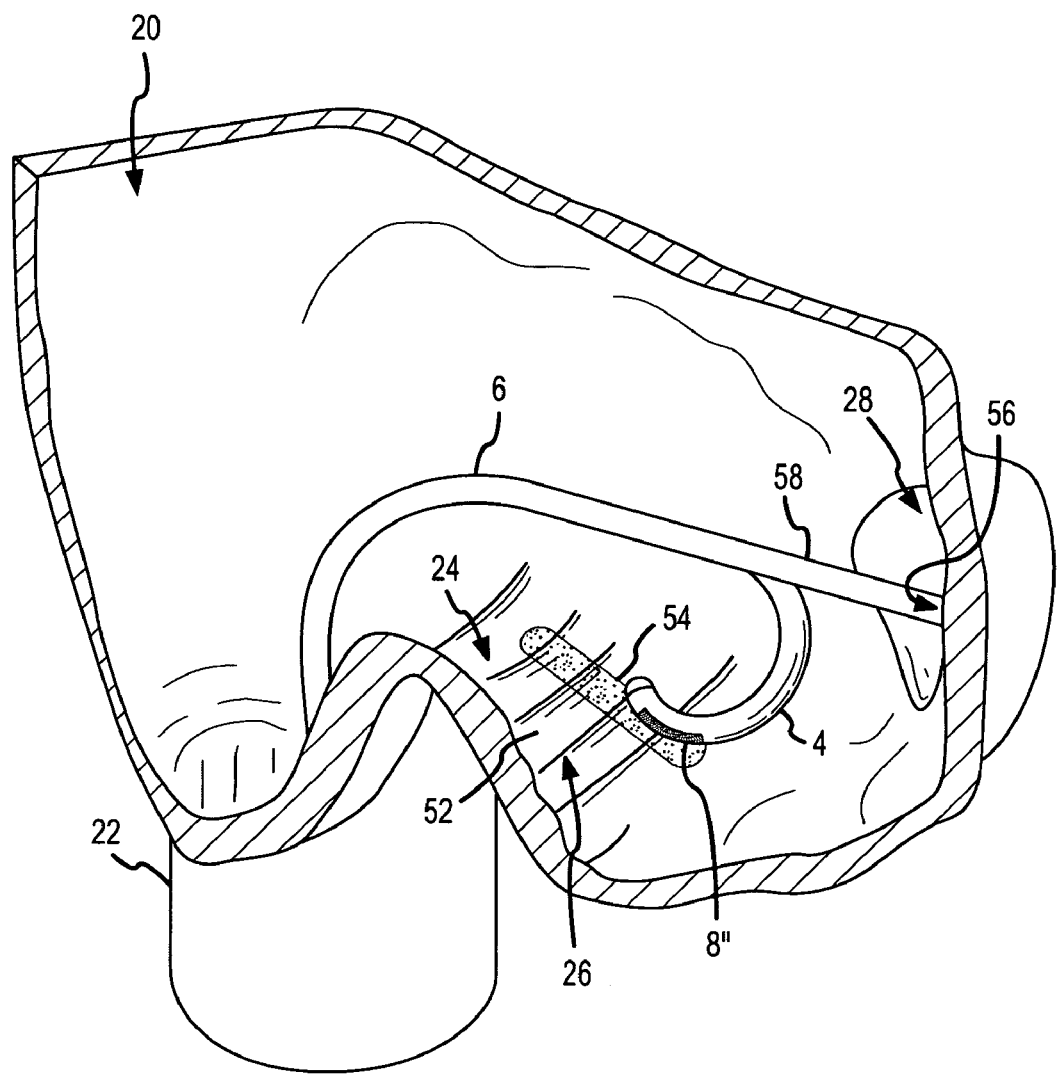
FIG. 15 is an isometric schematic of an alternate embodiment of the ablation catheter of the present invention with a mesh electrode depicted in situ in the right atrium.
Figure 16:
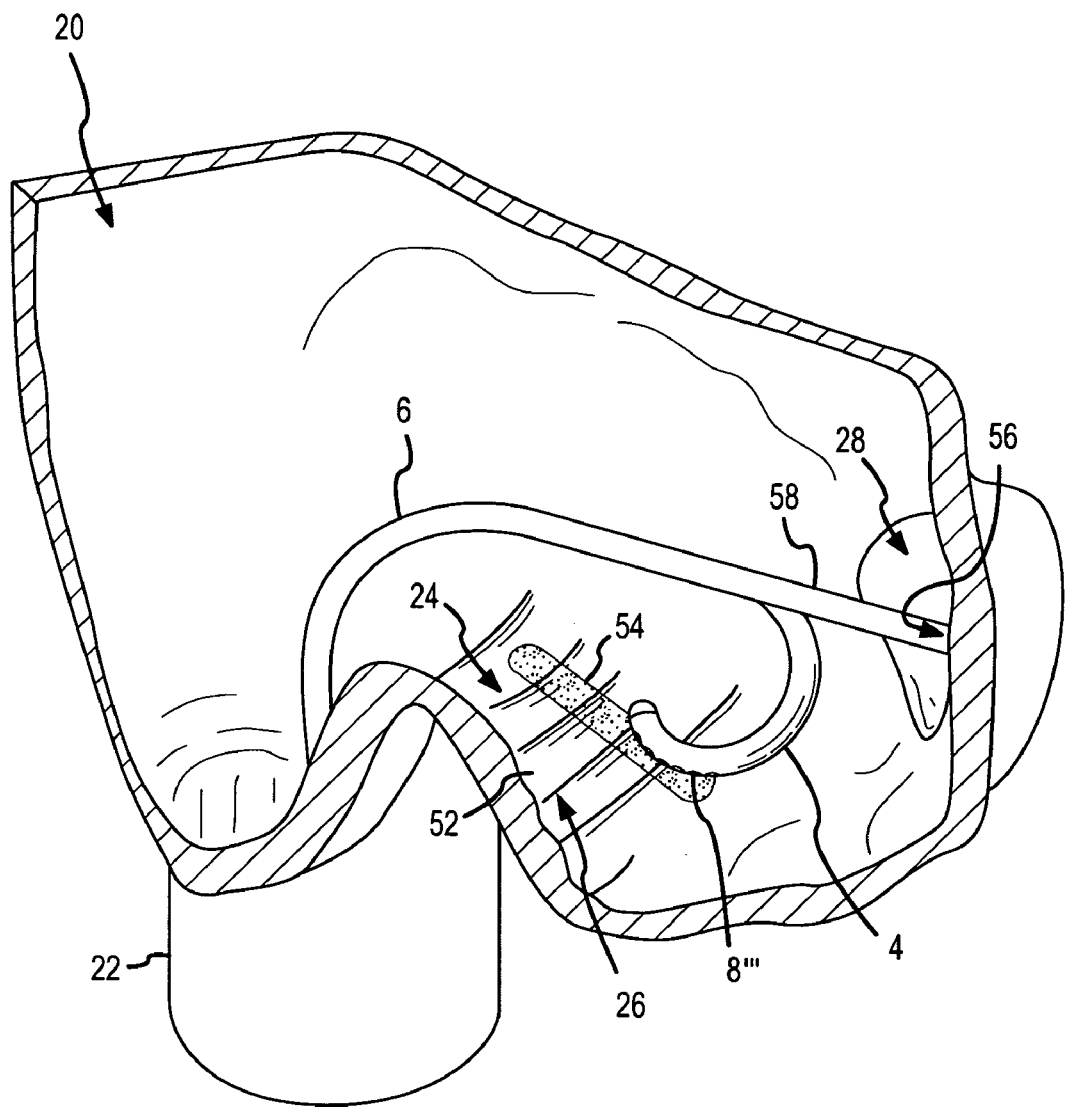
FIG. 16 is an isometric schematic of an alternate embodiment of the ablation catheter of the present invention with a virtual electrode depicted in situ in the right atrium.

Alternatively, the ablation electrode may embody other electrode forms to achieve particular desired results. For example, FIG. 15 depicts an embodiment of the present invention in which a mesh electrode 8" is integrated with the catheter wall 44 along a portion of the curved section of the catheter 4 and approaching the distal tip 18. A mesh electrode 8" of this exemplary type is disclosed more full in U.S. patent application Ser. No. 10/645,892, filed 20 Aug. 2003, and entitled Ablation Catheter and Electrode, the disclosure of which is hereby incorporated by references as though fully set forth herein. In this embodiment, the arc of travel of the curved section of the catheter 4 is greater than in other embodiments, for example, that of FIG. 1. This allows the linearly designed mesh electrode 8" in the catheter wall 44 to more fully lie against the tissue 52 on the isthmus 24 to create a linear lesion 54. Another embodiment of the present invention may incorporate a virtual electrode 8''' as depicted in FIG. 16. A virtual electrode 8''' supplies conductive fluid that is then energized with ablative energy to for a lesion in the tissue 52. A virtual electrode 8''' of this exemplary type is disclosed more full in U.S. patent application Ser. No. 10/608,297, filed 27 Jun. 2003, and entitled Ablation Catheter Having a Virtual Electrode Comprising Portholes and a Porous Conductor, the disclosure of which is hereby incorporated by references as though fully set forth herein. Again, the arc of travel of the curved section of the catheter 4 is greater than in other embodiments, for example, that of FIG. 1. This allows the linearly designed virtual electrode 8''' with its ports in the catheter wall 44 to apply fluid to the tissue 52 to create a linear lesion 54.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A device for ablating endocardial tissue, the device comprising
    a sheath for intravascular insertion into a cardiac cavity, the sheath defining
        a lumen;
        an entrance port located at a proximal end of the sheath; and
        an exit port located at a distal end of the sheath; and
    a catheter for insertion within the lumen of the sheath, wherein
        a distal tip of the catheter comprises an ablation electrode;
        the catheter is pliant compared to the sheath and, when residing with in the sheath, a distal portion of the catheter, proximal and adjacent to the distal tip, is constrained by the sheath; and
        the distal portion of the catheter embodies the shape of a preset curve and retains the preset curve when not otherwise constrained within the sheath; wherein
    when the catheter emerges from the exit port of the sheath,
        the distal portion of the catheter progressively furls to form a hook-shape with an increasing radius of curvature to gradually assume the preset curve;
        the catheter translates linearly as it furls; and
        the distal tip maintains an interface with and an orientation directed toward the endocardial tissue as the catheter furls and translates wherein the ablation electrode is placed in contact with the endocardial tissue along a linear path.

2. The device of claim 1, wherein the catheter further comprises a wire extending longitudinally through at least the distal portion of the catheter, and wherein the wire is shaped to form the preset curve.

3. The device of claim 1, wherein at least the distal portion of the catheter comprises a shape memory polymer to form the preset curve.

4. The device of claim 1, wherein the distal tip is more stiff than the distal portion of the catheter and the distal portion is more pliable than a proximal portion of the catheter.

5. The device of claim 1, wherein the radius of curvature of the distal portion of the catheter when forming the hook-shape is between 0.5 cm and 3 cm.

6. The device of claim 1, wherein the preset curve orients the distal tip of the catheter at an angle between 90° and 270° from the direction of orientation of the exit port at the distal end of the sheath.

7. The device of claim 1, wherein the exit port of the sheath comprises a slot on a side of the sheath and wherein the distal end of the sheath extends beyond the slot to form an anchoring member.

8. The device of claim 1, wherein the ablation electrode comprises a brush electrode.

9. The device of claim 1, wherein the ablation electrode comprises a virtual electrode wherein ablation energy is provided through perfusion of electrolytic fluid.

10. A catheter for ablating a surface of endocardial tissue, the catheter comprising
    an ablation electrode positioned on a distal end of the catheter;
    a proximal section; and a resilient curved section, proximal and adjacent to the distal end and distal and adjacent to the proximal section; wherein the curved section is sufficiently flexible to conform to a constraint, altering the curved section to assume a generally linear form, and to return to a preset curve when not otherwise constrained; and when gradually released from the constraint beginning at the distal end and progressing proximally, the curved section of the catheter progressively furls to form a hook-shape with an increasing radius of curvature to gradually assume the preset curve;

the distal end of the catheter translates linearly as it furls; and the distal end maintains a generally constant orientation as the catheter furls and translates and the ablation electrode travels along a linear path.

11. The catheter of claim 10, wherein the catheter further comprises a wire extending longitudinally through at least the curved section of the catheter, and wherein the wire is shaped to form the preset curve.

12. The catheter of claim 10, wherein at least the distal portion of the catheter comprises a shape memory polymer to form the preset curve.

13. The catheter of claim 10, wherein the distal end is more stiff than the curved section of the catheter and the curved section is more pliable than the proximal portion of the catheter.

14. The device of claim 10, wherein the radius of curvature of the curved section of the catheter when forming the hook-shape is between 0.5 cm and 3 cm.

15. The catheter of claim 10, wherein the ablation electrode comprises a brush electrode.

16. The catheter of claim 10, wherein the curved section defines an arc of between 90° and 270° between the exit port and the distal end.

* * * * *